United States Patent [19]
Czarniecki et al.

[11] Patent Number: 5,248,499
[45] Date of Patent: Sep. 28, 1993

[54] CONTROL OF MICROBIAL INFECTIONS IN TRANSPLANT PATIENTS

[75] Inventors: Christine Czarniecki, San Francisco, Calif.; Jon B. Klein, Louisville, Ky.; A. David Slater, Louisville, Ky.; Gerald Sonnenfeld, Louisville, Ky.

[73] Assignee: Genentech, Inc., South San Francisco, Calif.

[21] Appl. No.: 773,382

[22] Filed: Oct. 7, 1991

[51] Int. Cl.$^5$ .................. A61K 37/66; A61K 45/00
[52] U.S. Cl. .................. 424/85.2; 424/85.5; 424/85.1
[58] Field of Search .................. 424/85.2, 85.1, 85.5

[56] References Cited

FOREIGN PATENT DOCUMENTS

WO91/01727  7/1990  PCT Int'l Appl. .

OTHER PUBLICATIONS

Caselmann, W. H. et al., *Gastroenterology* 96: 449–455 (1989).
J. Kovarik et al., *Transplantation* 45(2): 402–405 (1988).
K. Takahashi et al., *Transplantation Proceedings* 19(5): 4089–4095 (1987).
Young, L. S., *J. Infec. Dis.* 147, 611 (1983).
Periti, P. and Mazzei, T., *Clin. Ther.* 8, 100 (1985).
Rubin, H. R. and Cosimi, A. B., "Infection in the Immunocompromised Host".
Rolston, K. and Bodey, G. P., *Hosp. Formul.* 22, 710 (1987).
Delgado, D. G. and Cobbs, C. G., *South. Med. J.* 73, 628 (1980).
Sabath et al. "Antimicrobial Agents".
Gould, C. L. and Sonnenfeld, G., *J. Interferon Res.* 7, 255 (1987).
Hershman et al., *J. Interferon Res.* 8, 367 (1988).
Hershman et al., *Infection and Immunity* 2412 Sep. (1988).
Hershman et al., *Microbial Pathogenesis* 4, 165 (1988).
Fennie et al., *Antiviral Res.* 10, 27 (1988).
Murphy et al., *Annals of Intern. Med.* 108, 36 (1988).
Zueva et al., UDC 618.98:579.561.2 863.
Schaffner, A. *J. Clin. Invest.* 76, 1755 (1985).
Guyre et al., *J. Steroid Biochem.* 30, 89 (1988).
Fuchs et al., *Am. J. Respir. Cell. Mol. Biol.* 1, 525 (1989).
Ijzermans et al., *Transpl. Proc.* XIX, 244 (1987).
Steiniger et al., *Transpl. Proc.* XIX, 4322 (1987).
McKenna et al., *Transplantation* 45, 76 (1988).
Ijzermans et al., *Transplantation* 48, 1039 (1989).
Rosenberg et al., *J. Immunol.* 144, 4648 (1990).
Kover et al., *Transplantation* 49, 148 (1990).
Kover, K. and Moore, W. V., *Transpl. Proc.* 22, 853 (1990).
Livingston et al., *J. Surg. Res.* 45, 37 (1988).
Baron et al., *JAMA* 266, 1375 (1991).
Didlake et al., *Transplantation* 45, 222 (1988).
McAllister et al., *Texas Heart Institute Journal* 13, 1 (1986).
Ono, K. and Lindsey, E. S., *J. Thoracic and Cardiovasc. Surg.* 57, 225 (1969).
Maluish et al., *J. Clin. Oncol.* 6, 434 (1988).
Biship, G. A. and Hall, B. M., *Transplantation (Baltimore)* 45 (5), 967 (1988).
Chang et al., *Transplantation (USA)* 49 (6), 1158 (1990).
Dupont et al., *Transplantation* 39 (2), 143 (1985).
Fahey et al., *Ann. Intern. Med.* (USA) 106 (2), 257 (1987).
Groenewegen et al., *Transplantation (USA)* 40 (1), 21 (1985).

(List continued on next page.)

*Primary Examiner*—Michael G. Wityshyn
*Assistant Examiner*—Choon P. Koh
*Attorney, Agent, or Firm*—Ginger R. Dreger

[57] ABSTRACT

The invention relates in general to the prevention and treatment of microbial infections in transplant patients. More particularly, the invention concerns the use of lymphokines, and specifically gamma interferon (IFN-γ) for the prophylaxis and treatment of microbial infections in transplant recipients, without increasing the incidence of graft rejections.

33 Claims, No Drawings

OTHER PUBLICATIONS

Halloran et al., *Transplantation* 46 (2 Suppl.), 68S–72S (1988).
Hancock et al., *Transplantation* 49 (2), 416 (1990).
Hao et al., *Transplantation* 49 (3), 609 (1990).
Hiestand et al., *Immunology (England)* 55 (2), 249 (1985).
Ho, M., *Birth Defects* 20 (1), 131 (1984).
Howard, R. J., *Surgery* 92 (2), 138 (1982).
Huber, C. and Irschick, E., *Bibl. Cardiol.* 43, 103 (1988).
Ijzermans et al., *Transplant. Proc. (USA)* 22 (4), 1941 (1990).
Kalman, V. K. and Klimpel, G. R., *Dell. Immunol. (USA)* 78 (1) 122 (1983).
Kahan et al., *Transplant. Proc. (USA)* 20 (2), 438 (1988).
Kupiec-Weglinski, et al., *Transplantation (USA)* 51 (2), 300 (1991).
Lin et al., *Transplant Proc.* 21 (1 Pt 2), 1874 (1989).
Liversidge et al., *Transplant. Proc. (USA)* 20 (3) Suppl. 4, 163 (1988).
Liversidge et al., *Immunology* (United Kingdom), 63 (2), 313 (1988).
Nakane et al., *Infect. Immun.* 56 (8), 2011 (1988).
Nickoloff et al., *Am. J. Pathol.* 131 (1), 12 (1988).
Raghavachar et al., *Exp. Hematol.* 14 (7) 621 (1986).
Reem et al., *Science* 221, 63 (1983).
Schellekens et al., *J. Gen. Virol.* (England) 65 (2), 391 (1984).
Suthanthiran et al., *Kidney Int.* 32 (3), 362 (1987).
Woloszczuk et al., *J. Coin. Chem. Clin. Biochem.* 24 (10) 729 (1986).
Woloszczuk et al., *J. Clin. Chem. Clin. Biochem.* (Germany, West) 24 (10) 729 (1986).
Steiner et al., *Transplant Proc. (USA)* 22 (4), 1857 (1990).
Yoshimura et al., *Nippon Geka Gakkai Zasshi* (Japan) 91 (8) 1011 (1990).
Yoshimura et al., *J. Clin. Immunol.* 9 (4), 322 (1989).
Yoshimura et al., *Transplant. Proc. (USA)* 20 (2) (Suppl. 2), 69 (1988).
Hirsch et al. NEJM, vol. 308, No. 25, (Jun., 1983) pp. 1489–1493.
Hirsch et al. The Biology of the Inteferon System Elsevier/North-Holland Biomed. Press (1981) pp. 339–342.

CONTROL OF MICROBIAL INFECTIONS IN TRANSPLANT PATIENTS

FIELD OF THE INVENTION

The present invention relates in general to the prevention and treatment of microbial infections in transplant patients. More particularly, the invention concerns the use of lymphokines, and specifically gamma interferon (IFN-γ) for the prophylaxis and treatment of microbial infections in transplant recipients, without increasing the incidence of graft rejections.

BACKGROUND OF THE INVENTION

It is well established in clinical experience that complications due to infections subsequent to allografting may result in the rejection of the allograft. The transplant patients often acquire microbial infections during their hospitalization or suffer infections attributable to microorganisms already colonizing the patient when admitted to the hospital. Microbial infection is considered to be a major limiting factor to the success of transplantation. This is particularly so because the immunosuppression required to prevent graft rejection greatly limits the success of conventional antimicrobial treatment in overcoming infections in transplant patients [Rolston et al., *Hospital Formul.* 22, 710 (1987); Glenn et al., *Rev. Infec. Dis.* 10, 42 (1988); Young, L. S., *J. Infec. Dis.* 147, 611 (1983); Delgado et al., *South Med. J.* 73, 627 (1980); Schimpff, S. C., In: *Current Concepts in Antibiotic Therapy for Febrile Episodes in Neutropenic Patients*, page 7, Eli Lilly and Co., Indianapolis, Ind. (1983)].

One possible way to control microbial infections in transplant recipients would be to use biological response modifiers (immunomodulators) to augment the immune response. This approach has been successfully carried out in animal models of trauma/infection not associated with transplantation, using IFN-γ treatment. Rodents that were subjected to several different models of trauma were immunosuppressed and showed increased mortality when infected with a variety of bacteria. Prophylaxis or therapy of the rodents with murine gamma interferon resulted in enhanced survival in several of the models. [Hershman et al., *Microb. Pathogen.* 4, 165 (1988); *J. Interferon Res.* 8, 367 (1988); *Clin. Exp. Immunol.* 73, 406 (1988); and *Infec. Immun.* 56, 2412 (1988); Livingston, D. H. & Malangoni, M. A., *J. Surg. Res.* 45, 37 (1988); copending U.S. Ser. No. 730,017, filed Jul. 12, 1991, which is a continuation of U.S. Ser. No. 265,411 filed Oct. 31, 1988, now abandoned.]

However, there are strong indications against using IFN-γ treatment to control infections in transplant patients.

It is known that cell membrane molecules encoded by genes of the major histocompatibility complex play an essential role in the interaction between cells of the immune system and a transplanted organ [Thorsby, E., *Transplant Proc.* 17, 29 (1987)]. Specifically, major histocompatibility complex (MHC) molecules of allografted tissue have the capacity to induce strong immune responses by activating T cells of the recipients. MHC class II molecules appear to be particularly strong transplantation antigens [Klempnauer, et al., *Transplant Proc.* 17, 1987 (1985)]. Since immunomodulation with IFN-γ treatment is known to include enhanced expression of MHC class II antigens [*Interferons and the Immune System*, Vilcek, J. & DeMaeyer, Eds., Elsevier Scientific Publishers, B. V., Amsterdam (1985)], there is a valid concern about the use of IFN-γ in the treatment of transplant patients. Indeed, IFN-γ (just as interleukin-2 (IL-2)) has been implicated as an important mediator of allograft rejection. IFN-γ and IL-2 receptor antibodies have been shown to prevent allograft rejection in experimental animals [Landolfo et al., *Science* 220, 176 (1985); Rosenberg et al., *J. Immunol.* 144, 4648 (1990); Kirkman, R. L. et al., *Transplantation* 40, 719 (1985)], and several studies have suggested that lymphokine, and in particular IL-2 and IFN-γ production can be correlated with rejection episodes in renal transplant recipients [Yoshimura, N. and Kahan, B. D., *Transplantation* 40, 661 (1985); Vie, H. et al., *Kidney Int.* 28, 553 (1985); Claesson, K. et al., *Transplantation* 38, 32 (1984)]. Woloszczuk et al., *J. Clin. Chem. Clin. Biochem.* 24, 729–34 (1986) observed increased serum levels of IFN-γ before rejection episodes, either directly related or unrelated to infections, and suggested that this observation would provide an easy and reliable method for monitoring of the immune status of transplant recipients. Systemic interferon administration in renal transplant recipients had been associated with an increased incidence of organ rejections [Kovarik, J. et al., *Transplantation* 45, 402 (1988)]. This serious adverse effect was concluded to be a contraindication to the use of interferons in the treatment of renal transplant patients [Baron et al., *JAMA* 266, 1375 (1991)].

Although the extent of involvement of lymphokines in graft rejection, and especially the mechanism by which they are involved are far from clear, and some studies of the rejection phenomena following IFN-Γ therapy have produced contradictory results [McKenna, R. M. et al., *Transplantation* 45, 76 (1988); Ijzermans et al., *Transplantation* 48, 1039 (1989); Rosenberg et al., supra: Kover et al., *Transplantation* 49, 148 (1990); Kover K. and Moore, W. V. in *Transplantation Proceedings* 22, 853–85 (1990)], the potential risk of accelerated graft rejection associated with IFN-γ administration has so far restrained physicians from using IFN-γ to treat infections in transplant patients.

The indications against the administration of lymphokines, and specifically IFN-γ to transplant recipients are even more apparent in view of our knowledge about the mechanism of action of cyclosporins and corticosteroids, which are the most commonly used immunosuppressants in transplantation.

The immunosuppressive action of cyclosporins in transplantation has been extensively studied, and is thought to be primarily due to their potent inhibition of lymphokine production by T cells. Cyclosporin A (CsA) has been shown to inhibit the transcription of IFN-γ and IL-2 mRNA in vitro [Kronke, M. et al., *Proc. Natl. Acad. Sci.* 81, 5214 (1984); Elliot et al., *Science* 226, 1439 (1984); Granelli-Piperno et al., *J. Exp. Med.* 163, 922 (1986)]. Several studies have shown a decrease in interleukin-2 (IL-2) and IFN-γ production of renal transplant recipients on cyclosporin A (CsA) treatment. For example, Yoshimura et al., *J. Clin. Immunol.* (USA) 9, 322–328 (1989) examined the in vivo effect of CsA administered with steroid on the capacity of peripheral blood mononuclear cells (PBMC) from kidney transplant recipients to generate cytokines and their gene expression at mRNA level. They found that combination therapy with CsA and steroid inhibits both IFN-γ and IL-2 gene expression.

A second, important group of immunosuppressants is the group of corticosteroids (glucocorticoids, GCC). It appears that the most important general cellular mechanisms by which they exert immunosuppressive actions may be their effects on the production and action of soluble factors, such as cytokines [Guyre et al., "Glucocorticoids and the immune system: activation of glucocorticoid-receptor complexes in thymus cells; modulation of Fc receptors of phagocytic cells." In: Progress in Research and Clinical Applications of Corticosteroids, Lee, H. J. and Walker, C. A., eds., Heyden & Son, Philadelphia, 14-27 (1981)]. It has also been reported that the production of IFN-γ is blocked by glucocorticoids [Guyre, et al., *J. steroid Biochem.* 14, 35-39 (1981); Kelso, A. and Munck, A., *J. Immun.* 133, 784-791 (1984)], while several parameters of monocyte activation by IFN-γ were either unaffected or enhanced [Girard, et al., *J. Immun.* 138, 3235-3241 (1987)]. A review of the effects of glucocorticoids on the production and actions of immune cytokines is, for example, provided by Guyre et al., *J. steroid Biochem.* 30, 89-93 (1988).

In summary, although the exact mechanism of the involvement of lymphokines, and specifically IFN-γ in graft rejection is not entirely understood, published results raise serious concerns about the applicability of lymphokine, e.g. IFN-γ therapy to prevent and fight microbial infection in transplant recipients, and appear to suggest that the potential negative effects of exogenous lymphokine administration could far outweigh any benefit resulting from the treatment of microbial infections.

SUMMARY OF THE INVENTION

The present invention is based on the unexpected finding that lymphokines, and specifically IFN-γ can be successfully used for the prophylaxis and treatment of microbial infections in transplant recipients under appropriate conditions, without significant increase in the incidence of rejection episodes. The present inventors have found that under clinical conditions, when following transplantation the transplant recipients are routinely subjected to long-term treatment with low, "maintenance" doses of cyclosporin, microbial infections can be successfully controlled (prevented or treated) by IFN-γ administration, without experiencing the potential deleterious effect of IFN-γ on graft survival.

In one aspect, the present invention relates to a method for the prophylaxis or treatment of microbial infections in transplant recipients comprising administering a therapeutically effective dose of an antimicrobial lymphokine to transplant recipients following transplantation under conditions such that the action of the lymphokine resulting in increased graft rejection is suppressed while retaining its antimicrobial activity. The antimicrobial lymphokine may, for example, be IFN-γ, IL-2 or their combination. The antimicrobial lymphokine is preferably administered to transplant recipients subjected to maintenance immunosuppressive therapy following transplantation. The maintenance immunosuppressive therapy preferably involves the administration of one or more immunosuppressants, such as cyclosporins and/or steroids.

In another aspect, the invention concerns a method of avoiding infection-associated graft rejection in transplant recipients, comprising administering a therapeutically effective dose of IFN-γ to transplant recipients subjected to maintenance immunosuppressive therapy following transplantation.

DETAILED DESCRIPTION OF THE INVENTION

The term "lymphokine" is used to describe soluble products of lymphoid cells, including proteins secreted by T cells upon activation by antigens or lectins. Examples of lymphokines include, but are not limited to, interferons-α, -β and -γ (IFN-α, IFN-β, IFN-γ), interleukin-2 (IL-2), interleukin-3 (IL-3), tumor necrosis factor-α (TNF-α), a colony stimulating factor (CSF-1, CSF-G, or CSF-GM), etc. The term "antimicrobial" activity includes antiviral, antibacterial, antiparasitic and antifungal activities. Typical representatives of lymphokines with antimicrobial activity are IFN-α, IFN-β, IFN-γ, IL-2, and TNF-α. Antimicrobial activity can be tested in established in vitro and in vivo models. Typical in vitro models are based on testing the activation of monocytes or neutrophils, and include the oxidative burst model described in Example 1 [see also Clifford, D. P., Repine, J. E., *Methods. Enzymol.* 105, 393 (1984)]. In vivo animal (e.g. rodent and non-human primate) models suitable for evaluating the antiviral, antibacterial, antiparasitic, and antifungal activities of lymphokines, e.g. interferons, such as IFN-γ are also well known in the art, and will be discussed hereinbelow.

As used herein, "gamma interferon", "interferon-γ" or "IFN-γ" refers variously to all forms of (human and non-human animal) gamma interferons capable of activation of immune response against infection. The above terms are meant to specifically include IFN-γ in a mature, pro, met or des(1-3) (also referred to as desCys-TyrCys IFN-γ) form, whether obtained from natural source, chemically synthesized or produced by techniques of recombinant DNA technology.

In nature, the production of IFN-γ is induced in T lymphocytes by foreign antigens to which the T cells are sensitized. Under certain conditions, natural killer (NK) lymphocytes may also produce IFN-γ. The recombinant production of IFN-γ was first reported by Gray, Goeddel and co-workers [Gray et al., *Nature* 295, 503-508 (1982)], and is the subject of U.S. Pat. Nos. 4,762,791, 4,929,544, 4,727,138 and 4,925,793. The recombinant IFN-γ of Gray and Goeddel, as produced in *E. coli*, consisted of 146 amino acids, the N-terminal portion of the molecule commencing with the sequence CysTyrCys. It has later been found that the native IFN-γ (i.e., that arising from mitogen induction of human peripheral blood lymphocytes and subsequent purification) is a polypeptide which lacks the CysTyrCys N-terminus assigned by Gray et al., supra.

Non-human animal interferons, including IFN-γ, are, for example, disclosed in EP 88,622 published Sep. 14, 1983.

The terms "gamma interferon", "interferon-γ" or "IFN-γ" include variously glycosylated forms and other variants and derivatives of such interferons, whether known in the art or will become available in the future. Examples of such variants are alleles, and the products of site directed mutagenesis in which residues are deleted, inserted and/or substituted (see, for example, patent application No. EP 146,354, published Jun. 26, 1985).

The antiviral activity of interferons, and in particular IFN-γ, has been demonstrated against a large number of viruses, in numerous in vitro and in vivo models.

Neumann-Haefelin et al., *Med. Microbiol. Immunol.* 174, 81 (1985) found that recombinant human IFN-γ (rHuIFN-γ) prevented Herpes simplex (HS) keratitis in African green monkeys.

Van der Meide et al., *Antiviral Research*, Suppl. 1. 199 (1985) compared the in vivo antiviral effects of human IFNs-α, -β and -γ on vaccinia virus infection in rhesus monkeys. Infection was monitored by observation of skin lesions (appearance and diameter of papules and pustules). The results showed significant reduction in lesion severity for the groups intramuscularly treated with natural or recombinant HuIFN-γ.

The in vivo antiviral activity of recombinant murine IFN-γ (rMuIFN-γ) was, for example, evaluated by Shalaby et al., *J. Interferon Research* 5, 339 (1985), in a murine model of emcephalomyocarditis (EMC) virus infection. The results demonstrated the ability of rMuIFN-γ to protect mice against EMC virus infection. Similar results were reported by Sim, I. S. and Cerruti, R. L., *Antiviral Res.* 8, 209 (1987).

Treatment with rMuIFN-γ prior to infection with cytomegalovirus (MCMV) was reported to significantly reduce mortality in a murine model [Fennie et al., *Antiviral Res.* 10, 27 (1988)].

Further studies examined the efficacy of various immunomodulators, including rMuIFN-γ in mouse models of experimental infection with Herpex simples type 2 (HSV-2) virus, Banzi flavi virus, Venezuelan equine encephalitis (VEE) virus, and Caraparu bunya virus [Pinto et al., *Intern. J. Immunopharmacology* 10, 197 (1988)].

The efficacy of recombinant rat IFN-γ (rRatIFN-γ) against pseudorabies virus (PRV) infection in immunologically impaired and immunosuppressed rats was demonstrated by Schijns et al., *J. Gen. Virol.* 69, 1979 (1988).

Although the mechanism by which the interferons produce their antiviral actions is not entirely understood, it is known that instead of directly inactivating viruses, they act indirectly through virus-susceptible cells. The wide antiviral range of interferons, including IFN-γ, is thought to be due to their ability to modulate multiple biochemical pathways that that have different antiviral effects and act on different parts of the viral replication cycles [Pestka et al., *Ann. Rev. Biochem.* 56, 727 (1987); Samuel, C. E., *Prog. Nucl. Acid Res. Mol. Biol.* 35, 27 (1988); Jacobsen, H., *Arzneim. Forsch. Drug Res.* 36, 512 (1986)].

Numerous studies have demonstrated the ability of interferons to control, and particularly to prevent bacterial infections.

rMuIFN-γ and rRatIFN-γ were tested and found efficacious in various simulated wound bacterial infection models, including surgically stimulated and burn wound infection models [Hershman et al., *Clin. Exp. Immunol.* 72, 406 (1988); Hershman et al., *Microbial Pathogenesis* 165 (1988); Hershman et al., *J. Interferon Res.* 8, 367 (1988)]. The use of IFN-γ for the treatment of trauma-associated sepsis is reported by Herman, M. J. et al., *Infection and Immunity* 56, 2412 (1988), and is disclosed in copending U.S. application Ser. No. 730,017, filed Jul. 12, 1991, which is a continuation of application Ser. No. 265,411, filed Oct. 31, 1988, now abandoned.

IFN-γ was, for example, shown to be efficacious in the prophylaxis and treatment of *Klebsiella pneumoniae, Pseudomonas aeruginosa, Staphylococcus aureus, Chlamydia trachomatis, Mycobacterium itracellulare, Mycobacterium tuberculosis, Francisella tularensis, Salmonella typhimurium, Lysteria monocytogenes* infections, in various in vitro nd in vivo models of infection.

Although not completely understood, the mechanism of action of interferons, e.g. IFN-γ is believed to involve a reduced ability of the bacteria to enter interferon treated cells.

The parasitic infections successfully controlled (prevented and/or treated) by IFN-γ include *Leshmania donovani* infections [see e.g. Murray et al., *J. Clin. Invest.* 83, 1253 (1989)] and *Toxoplasma gondii* [McCabe et al., *J. Infect. Dis.* 150, 961 (1984)], and malaria in various Plasmodium infection models.

In vitro data suggest that immune cells (macrophages, neutrophils, etc.) are activated by incubation with IFN-γ to kill fungi (*C. albicans, H. capsulatum, B. dermatitis, P. brasiliensis*) by oxidative as well as non-oxidative mechanisms as efficiently as other classes of microbial pathogens [see e.g. Brummer et al., *J. Immunol.* 140, 2786 (1988)]. Shear et al., *J. Acquired Immune Deficiency Syndromes* 3, 943 (1990) reported the efficacy of IFN-γ in the prophylaxis and treatment of steroid-induced *Pneumocystis carinii* (an organism occasionally referred to as a parasite) pneumonia (PCP) in rats.

The recent knowledge of the mechanisms of action and clinical application of interferons, including IFN-γ is summarized by Baron et al., in *JAMA* 266, 1375 (1991).

IFN-γ is known to have a narrow host range, therefore, IFN-γ homologous to the animal to be treated should be used. In human therapy, the desCysTyrCys variant of the sequence shown, for example, in U.S. Pat. No. 4,717,138, and its counterpart U.S. Pat. No. 77,670 (published Apr. 27, 1983) is preferably employed, and optionally the C-terminal truncated variant in which the last 4 residues are deleted in post-translational processing.

"Interleukin-2" or "IL-2" (originally named T cell growth factor) was first described by Morgan, D A. et al., *Science* 193, 1007 (1976). The production of IL-2 by cultivating human peripheral blood lymphocytes (PBL) is, for example, described in U.S. Pat. No. 4,401,756. The recombinant production of IL-2 is, for example, reported by Taniguchi et al., *Nature* 302, 305 (1983) and Devos et al., *Nucleic Acid Res.* 11, 4307 (1983). "Interleukin-2" or "IL-2" refers variously to all forms of IL-2 as are known to be biologically active in accepted IL-2 assays, including alleles and variants obtained by substitution, insertion or deletion of one or more amino acids in the native amino acid sequence, for example as described in U.S. Pat. No. 4,518,584. The antimicrobial activity of IL-2 is, for example, described in PCT Applications Publication Nos. WO 85/05124 (published Nov. 21, 1985) and WO 85/03948 (published Sep. 12, 1985), EP 147,819 (published Jul. 10, 1985), EP 118,617 (published Sep. 19, 1984), EP 118,977 (published Sep. 19, 1984), EP 132,754 (published Feb. 13, 1985), EP 94,317 (published Nov. 16, 1983), and in U.S. Pat. Nos. 4,407,945 and 4,473,642.

"Tumor necrosis factor-α" or "TNF-α" was first described by Carswell et al., *Proc. Natl. Acad. Sci. USA* 72, 3666 (1975). The production of TNF-α by recombinant DNA technology was reported by Pennica et al., *Nature* 312, 724 (1984), and is, for example, disclosed in EP 168,214 (published Jan. 15, 1986).

The treatment of bacterial infections in mammalian hosts with lymphokines, and specifically with TNF-α alone or in combination with IL-2 or with IFN-γ is described in U.S. Pat. No. 4,879,111.

The term "immunosuppressed" patient is used to denote a patient with impaired host defenses who is at risk of developing opportunistic infections. In transplant patients immunosuppression is the result of immunosuppressive therapy which is unavoidable for the successful performance of transplantation.

The terms "transplantation" and "transplant" are used herein in the broadest sense, and include solid and non-solid organ and tissue transplantations and transplants, such as liver, heart, kidney, and heterologous and autologous bone marrow transplantations/transplants.

The term "immunosuppressive therapy" is used in the broadest sense, and may involve the administration of immunosuppressive drugs (also referred to as "immunosuppressants"), such as cyclosporins, corticosteroids, cytotoxic immunosuppressants, antilymphocyte globulins, but also covers irradiation and associated chemotherapy. The particular immunosuppressive therapy is dependent on the nature of transplant.

Typical immunosuppressive therapy used to avoid graft rejection in recipients of solid organ transplants involves the use of cyclosporins, corticosteroids, and further immunosuppressive agents such as azathioprine, cyclophosphamide, and methotrexate. Recipients of bone marrow transplants are usually subjected to extensive irradiation and chemotherapy prior to transplantation.

Corticosteroids such as prednisone and dexamethasone, are known to have the most global immunosuppressive effects, and are able to alter almost every aspect of the host defense system. They impair the mobilization, adherence, phagocytosis, and bactericidal activity of neutrophils, monocytes, and macrophages, depress T- and B-lymphocyte activity, diminish production of interferons and other cytokines, and alter the gastrointestinal flora. Their greatest effect is on leukocyte responses. Steroid treatment greatly increases the patient's susceptibility to a variety of bacterial, viral, fungal, or parasitic infections, and activates latent endogenous infections. According to clinical practice, high doses of steroids are usually well tolerated up to about three weeks, but after that the incidence of various, often life threatening, infections substantially increases.

Immunosuppressive agents often used in combination with corticosteroids, including cyclophosphamide, azathioprine and methotrexate, are also known to produce defects in host defenses and to enhance the risk of infectious complications.

"Cyclosporins" are a group of biologically active metabolites produced by *Tolypocladium inflatum Gams* and other fungi imperfecti. The major components, cyclosporins A and C, are non-polar cyclic oligopeptides with immunosuppressive properties. In particular, Cyclosporin A (CsA) is widely used in clinical practice as immunosuppressant. Synthetic cyclosporin analogues, such as Cyclosporin G (CsG) [Sandoz, Inc.; see McKenna et al., *Transplantation (USA)* 47, 343–348 (1989)], (Nvasup 2)-CS and (Valsup 2)DH-CS [Hiestand et al., *Immunology* 55, 249–255 (1985)] are also known. The term "cyclosporin" as used throughout the specification and claims includes all naturally occurring cyclosporins and their synthetic analogues and derivatives, either known in the art or hereinafter produced, provided that they have immunosuppressive properties similar, in kind, to those of Cyclosporin A. Cyclosporins are advantageous in that they are more specific in their action than corticosteroids. Their activity appears to be specifically directed against the T-lymphocyte helper/inducer lymphocyte subpopulation, without any direct effect on functioning B-cells, monocytes, macrophages, neutrophils and natural killer (NK) cells.

Radiation therapy (like cytotoxic drugs) has the greatest effect in suppressing the development of new immune response. Although, if the treatment is carefully administered, infections that can be directly attributed to radiation therapy are relatively rare, total body irradiation often results in granulocytopenia.

According to clinical experience, the cumulative effects of various immunosuppressive therapies/agents may far exceed the effects of each treatment alone.

A typical prophylactic (pre-operative and maintenance) immunosuppressive protocol used in renal (and with some modifications in heart) transplant patients includes the administration of Cyclosporin A, azathioprine and corticosteroids. According to a representative protocol, Cyclosporin A is administered orally, in a pre-operative dose of 12 mg/kg, while the initial post-operative dose is 8 mg/kg/day, and is adjusted by blood level. Following the same protocol, azathioprine is administered in a pre-operative i.v. dose of 3 mg/kg and in a post-operative dose of 1.5 mg/kg/day, which is decreased if the white blood count (WBC) drops below 3,000. The daily dose of steroids is 2 mg/kg/day on days 0, 1 and 2, and is gradually decreased to about 0.15 mg/kg/day, which is typically reached at or about day 120.

In some situations, an anti-lymphocyte preparation (e.g. anti-CD3 [OKT3], anti-CD4 [OKT4], anti-CD8, anti-CD11a, 11b, or 11c, anti-CD18, anti-lymphocyte globulin, anti-IL-2 receptor) is administered to the patient immediately after transplantation. This permits the discontinuance of cyclosporin administration, and some experts believe may induce partial tolerance of the graft. The risk of infection, particularly Cytomegalovirus (CMV) and Epstein-Barr virus (E-B) associated lymphoproliferative syndromes, is very high in this situation.

When rejection of the transplant is diagnosed by biopsy, clinical impression or any other diagnostic method known in the art, anti-rejection therapy is initiated. This might include the administration of high doses of steroids, anti-lymphocyte therapy or their combination. For example, renal transplant recipients are typically treated with a 500 mg/kg/day intravenous dose of Solumedrol (methylprednisolone 21-succinate sodium salt, Upjohn) for four days following the diagnosis of mild rejection. If the rejection is moderate or severe, an anti-CD3 [OKT3] murine monoclonal antibody (Orthoclone) may, for example, be administered in a 5 mg/day i.v. dose for about 10 to 14 days.

It will be understood that although the prophylactic and anti-rejection protocols outlined above are typical of many transplant centers, treatment may considerably vary by program philosophy, the type of organ transplanted, and the patient's vary from about 1 to about 20 mg/kg/day. The doses required for liver and heart transplants are usually higher than for kidney and bone marrow transplants. The use of lymphokines, and particularly IFN-γ for the prophylaxis or treatment of microbial infections in transplant patients is envisioned in conjunction with any of the prophylactic or anti-rejection protocols used in the clinical practice. In transplant patients, who do not receive anti-lymphocyte prophylaxis, and are administered cyclosporin and high doses of steroids, lymphokine (IFN-γ) administration should typically be initiated at the time of transplantation, and should typically be maintained up to about 40 days thereafter. In patients receiving prophylactic anti-lymphocyte therapy, the administration of lymphokines (e.g. IFN-γ) can typically be initiated at the time of transplantation and continued for about 7 to 21 days after the anti-lymphocyte therapy is concluded. When the monitoring of patient suggests that rejection is occurring, lymphokine (IFN-γ) administration can be initiated parallel with conventional immunosuppressive therapy (e.g. high doses of steroids) and should be maintained for at least about two weeks, to prevent infections associated with impaired immune response.

The lymphokines, such as IFN-γ, IL-2, as well as the immunosuppressants, such as cyclosporins are usually administered in the form of pharmaceutical compositions comprising an effective amount of the active ingredient in admixture with a suitable pharmaceutically acceptable vehicle and optionally other pharmaceutically acceptable additives.

The term "pharmaceutical composition" refers to preparations which are in such form as to permit the biological activity of the active ingredients to be unequivocally effective, and which contain no additional components which are toxic to the subjects to which the composition would be administered. Such pharmaceutical compositions may be prepared and formulated in dosage forms by methods known in the art; for example, see Remington's Pharmaceutical Sciences, Mack Publishing Company, Easton, Pa., 15th Edition 1975.

"Pharmaceutically acceptable" excipients (vehicles, additives) are those which can reasonably be administered to a subject mammal to provide an effective dose of the active ingredient employed. Typical vehicles include saline, dextrose solution, Ringer's solution, etc. but non-aqueous vehicles may also be used.

Lymphokines may be administered to a subject mammal, such as human, via any of the accepted modes of administration for such agents, including subcutaneous and parenteral administration. Examples of parenteral administration routes are intravenous, intrapulmonary, intraarterial, intramuscular, and intraperitoneal administration. The actual route of administration will depend on a number of considerations, including the nature of infection to be treated, if the administration is initiated after the onset of infection. Usually subcutaneous or intravenous administration is preferred, but for the treatment of lung (*P. carinii*) infections intrapulmonary administration may be best suited.

For parenteral administration, the lymphokines are generally formulated in a unit dosage injectable (e.g. solution, suspension, emulsion) form.

The formulation of IFN-γ is preferably liquid, and is ordinarily a physiological salt solution or dextrose solution, together with conventional stabilizers and/or excipients. IFN-γ compositions may also be provided as lyophilized powders. A typical formulation may contain IFN-γ ($20 \times 10^6$ U) at 1.0 or 0.2 mg/ml, 0.27 mg/ml succinic acid, and disodium succinate hexahydrate 0.73 ml/injection at pH 5.0. Preferred liquid formulations comprising non-lyophilized IFN-γ are disclosed in copending U.S. Ser. No. 07/514,392, filed Apr. 25, 1990. Such liquid formulations have a pH of about 4.0 to 6.0 and comprise a stabilizing agent and a non-ionic detergent. For intrapulmonary delivery, IFN-γ is typically administered as a dispersion comprising a therapeutically effective amount thereof. The dispersion preferably is an aerosol formulation, in which greater than about 15% of the particles have a particle size of from about 0.5 μm to about 4 μm (see EP 257,956 published Feb. 3, 1988, and U.S. application Ser. No. 897,962, filed Aug. 19, 1986).

IFN-γ is preferably administered according to the present invention subcutaneously at doses from about 0.01 to about 0.1 mg/m²/day as long as necessary to treat the infection. The frequency of administration varies depending on the nature of infection, and the patient's condition, and preferably is between daily and once a week.

IL-2 containing pharmaceutical compositions suitable for reconstitution in a pharmaceutically acceptable aqueous vehicle are disclosed in PCT Application Publication No. WO 85/04328.

In a pharmacological sense, in the context of the present invention, an "effective amount" of a lymphokine, such as IFN-γ and/or IL-2 refers to an amount effective in control of microbial infections. In this context, the term "control" is used to include both prophylaxis and treatment of such infections. Accordingly, IFN-γ may be administered prophylactically (i.e prior to the appearance of the infection), or therapeutically (i.e. after appearance of the infection), the prophylactic application being preferred.

The determination of the exact doses in view of the patient's condition, and the desired frequency is well within the skill of a skilled artisan. Immunologically effective doses may generally be determined for a particular application according to the procedure of Maluish et al., *J. Clin. Oncol.*, 6, 434–435 (1988).

The term "microbial infection" and its grammatical variants are used to refer to any infections occurring in transplant patients that can be controlled by lymphokine, e.g. IFN-γ or IL-2 treatment. Such microbial infections are primarily the opportunistic infections stemming from the depressed immunity of transplant recipients due to immunosuppressant treatment, also common in other immunocompromised hosts such as AIDS patients [Gottlieb, et al., *Ann. Intern. Med.* 99, 208 (1983); Periti, P. and Mazzei, T., *Clinical Therapeutics* 8, 100 (1985)]. Opportunistic pathogens that frequently cause infectious complications in immunocompromised patients are bacteria, such as *Staphylococcus aureus*, Streptococci, *Pseudomonas aeruginosa, Escherichia coli, Klebsiella pneumoniae, Haemophilus influenzae, Legionella pneumophila, Salmonella* species, *Aeromonas hydrophila*, Marine vibrios (halophilic), *Nocardia* species, *Mycobacterium tuberculosis;* fungi, such as *Candida* species, *Torulopsis* species, *Aspergillus* species, Zygomycetes, *Cryptococcus neoformans, histoplasma capsulatum;* viruses, such as Herpes simplex, Varicella zoster, Cytomegalovirus (CMV), Epstein-Barr (E-B) virus, Hepatitis B virus; parasites, such as *Toxoplasma gondii, Strongiloides stercoralis, Pneumocystis carinii* (the latter organism is also thought to be a fungus) [Periti, P. and Mazzei, T., "Infections in Immunocompromised Patients" in *Clin. Ther.* 8, 100–117 (1985) and Ho, M., "Human cytomegalovirus infections in immunosuppressed patients." In: Cytomegalovirus: Biology and Infection, 171-204, Plenum Press, New York, (1982)]. A common clinical presentation of such infections is the occurrence of pneumonia caused by *Pneumocystis (P.) carinii,* or *Legionella* species; however, other usual bacterial (*Salmonella* species, *Lysteria monocytogoenes*), mycobacterial, fungal and protozoa infections, listed above or otherwise known, can also be prevented or treated with IFN-γ in accordance with the present invention.

The potentials of IFN-γ in the treatment microbial infections in immunocompromised transplant recipients are supported by reports that in addition to its profound effect on immune responses, IFN-γ enhances phagocytosis, oxidative capacity, chemotaxis and microbial capacity of monocytes and macrophages in vitro from patients with AIDS [Murray et al., N. Engl. J. Med. 310, 883 (1984)].

Some of the above-listed and further microbial infections are also directly associated with the surgical trauma of transplantation. Such trauma-associated infections typically include bacterial infections caused by Gram-positive bacteria, such as Staphylococcus aureus, Streptococcus faecalis, Pneumococci, anhaemolytic Enterococci, Sarcina species, and haemolytic Streptococci; and Gram-negative bacteria such as Escherichia coli, Pseodomonas species, Klebsiella species, Proteus species, Enterobacter cloacae, coliform bacteria, Serratia species, Citrobacter species, and Providencia species [Allgower et al., Surg. Clin. N. Am. 60, 133-144 (1980)].

Lymphokines, and specifically IFN-γ, can be co-administered with each other and other antimicrobial agents or therapeutics used in the treatment of transplant patients. Co-administration includes simultaneous or successive administration. Oral antimicrobial agents that, despite suppression of aerobic flora, preserve colonization resistance include, for example, co-trimoxazole, nalidixic acid, oxolinic acid, pipemidic acid, framycetin, polymyxin B, colistin, nystatin, amphotericin B, clotrimazole, miconazole, ketokonazole. Prophylaxis with co-trimoxazole has, for example, become a standard procedure in patients at high risk of acquiring P. carinii pneumonia [Russe et al., J. Antimicrob. Chemother. 8, 87 (1981)]. Oral antimicrobial agents that decrease colonization resistance include, for example, aminoglycosydase antibiotics, e.g. neomycin, paromomycin, kanamycin, bekanamycin, ribostamycin, dibekacin, tobramycin, amikacin, gentamicin, sisomicin, netilmicin, bacitracin, vancomycin. Aminoglycosidase antibiotics are usually administered with a beta-lactam (penicillin and/or cephalosporin) antibiotic. Penicillin antibiotics include penicillin, carbenicillin, ampicillin, amoxacillin, methicillin, oxacillin, cloxacillin, dicloxacillin, nafcillin, thienamycin, piperacillin, azlocillin, mezlocillin, etc. Cephalosporin antibiotics include, e.g. cephalexin, cephradine, cefaclor, cefadroxil, cefatrizine, cefaparole, cefroxadine, cephalothin, cephaloridine, cefalozin, cefonicid, cefametazole, etc. The antimicrobial therapy herein may be combined with the administration of any of such known antimicrobial agents and further therapeutics traditionally used in the treatment of transplant patients. For further details see Periti, P. and Mazzei, T., supra and Cushing, Surg. Clin. N. Am. 57, 165 (1977).

Further details of the invention are illustrated in the following non-limiting Examples.

EXAMPLE 1

Administration of IFN-γ to Heart Transplant Recipients

I. Materials and Methods

Rats Lewis strain rats and AC strain rats (200-250 g) were obtained from Charles River Laboratories, Portage, Mich. Transplantation procedure All rats were anesthetized with 10% phenobarbital sodium solution. The Lewis strain rats each received 1 mg of gentamicin via the intramuscular route. AC rats received 100 units of heparin intravenously. The heart was removed from the AC rat, flushed through the aorta with saline at 4° C., and placed into an iced saline solution. Heterotopic transplantation of the AC rat heart into the abdomen of the Lewis rat was carried out by the technique of Ono and Lindsey [J. Thorac. Cardio. Surg. 57, 15 (1969)]. Standard recovery procedures were used, and the animals were examined daily for palpable heart beat. Rejection was considered complete on the last day the heart beat was palpable. The animals were sacrificed on the day following rejection, or, if there was no rejection, 20 or 45 days after the transplantation took place. Transverse sections of the midportion of the right and left ventricular chambers were stained with hematoxylin and eosin. Slides were examined and a histologic rejection score from 0-10 was assigned using the Texas Heart Institute rejection scale [McAllister, et al., Texas Heart Inst. J. 13, 1 (1986)] by a pathologist experienced in grading heart transplantation rejection and blinded completely to the experimental protocol.

Cyclosporin treatment All transplanted rats received a dose of 20 mg/kg/day on the day of transplantation as well as 1 and 2 days post-transplantation. This dose controls rejection so that the heart transplants are rejected 45 days post-transplantation [Hershman, et al. Infec. Immun. 56, 2412 (1988); and Clifford, D. P. & Repine, J. E., Methods Enzymol, 105, 393 (1984)]. Some transplanted rats received additional "maintenance" cyclosporin treatment of 8 mg/kg/day by gavage feeding beginning on day 3 post-transplantation and continuing throughout the experiment.

IFN-γ treatment Recombinant rat IFN-γ was purchased from Amgen Biologicals, Thousand Oaks, Calif., and had a specific activity of $4 \times 10^8$ units/mg protein. IFN-γ was given to the rats as described for each individual experiment.

Measurement of oxidative burst Neutrophils were separated from whole blood of the rats by density centrifugation using 1119 isolation medium (Sigma Chemical Company, St. Louis, Mo.). F-Met Leu-Phe (FMLP) was used to trigger respiratory burst, and the production of superoxide was measured by fluorometric methods [Clifford et al., Methods Enzymol.105, 393 (1984)].

Statistical analysis When sample sizes for each group were equal, the Student t Test was used for analysis of the data. When sample sizes were different, the Behrens-Fisher t Statistic with the Welsh df correction was used for analysis of the data.

All experimentation was carried out in compliance with the "principles of Laboratory Animal Care" formulated by the National Society for Medical Research. All animals were housed in an AAALAC facility under NIH guidelines under the direct supervision of a veterinarian.

II. Effect of IFN-γ on rejection of the heart transplant

Lewis strain recipient rats were received 20 mg/kg/day of cyclosporin on the day of transplant and for two days following transplantation. The heart of an AC strain rat was transplanted into the abdomen of each recipient. The rats in the control group did not receive any additional treatment. The 20 mg/kg/day dose of cyclosporin administered as described is known to control rejection so that hearts are rejected 45 days post-transplantation (Hershman, et al., supra).

Experimental rats each received 750 units of IFN-γ per day via the intramuscular route on the day of transplant and for 3 additional days. The results set forth in Table 1 show that the rats treated with IFN-γ showed a much accelerated rejection compared to controls.

TABLE 1

Effect of IFN-γ treatment on retention of heart transplants by rats

| Treatment | N | Mean Days to Rejection | P |
|---|---|---|---|
| Control | 10 | 44.7 | — |
| 750U IFN-γ | 5 | 11.0 | <0.05 |

(In a third group, transplantation was performed on Lewis strain recipient that did not receive cyclosporin, and were administered IFN-γ as described above. This group could not be evaluated because of early rejection.)

III. Effect of maintenance doses of cyclosporin on IFN-γ mediated enhanced rejection of the heart transplant.

A. Effect of maintenance doses of cyclosporin on rejection of transplanted hearts Each of the Lewis strain recipient rats received 20 mg/kg/day of cyclosporin on the day of transplantation as well as one and two days post-transplantation. The rats received additional "maintenance" doses of 8 mg/kg/day cyclosporin beginning on the 3rd day after transplantation and continuing throughout the course of the experiment. Groups of rats were sacrificed 20 days or 45 days post-transplantation. No difference in histological mean rejection score was noted at 20 and 45 days post-transplantation, as shown in Table 2.

TABLE 2

Effect of "maintenance" cyclosporin on rejection of transplanted hearts

| Time of Sacrifice | N | Mean Rejection Score | P |
|---|---|---|---|
| 20 days post-transplant | 10 | 1.0 | — |
| 45 days post-transplant | 10 | 1.2 | NS |

NS = not significant

B. Effect of maintenance cyclosporin treatment on IFN-γ enhanced rejection of heart transplants All rats received 20 mg/kg/day cyclosporin beginning on the day of transplantation and continuing for two additional days. The rats also received "maintenance" doses of 8 mg/kg/day of cyclosporin beginning on the third day post-transplantation and continuing until sacrifice. Experimental rats were treated with either 750 units/day or 7,500 units/day of IFN-γ via the intramuscular route starting on the day of transplantation and for three additional days. Transplanted hearts did not show complete rejection (stop beating) throughout the course of the experiment i.e. the hearts were not rejected by 45 days post-transplantation. Mean rejection scores were increased significantly only with the 750 units dose of IFN-γ at 20 days, but there was no significant difference at 45 days after transplantation (Table 3).

TABLE 3

Effect of "maintenance" cyclosporin treatment on IFN-gamma enhanced rejection of heart transplants

| Treatment | MRS (20 Days) | N | P | NRS (5 Days) | N | P |
|---|---|---|---|---|---|---|
| None | 1.0 | 10 | — | 1.2 | 10 | — |
| 750U IFN-γ | 3.0 | 10 | <0.05 | 1.5 | 5 | NS |
| 7,500U IFN-γ | 2.9 | 5 | NS | 2.2 | 4 | NS |

MRS = mean rejection score, using the Texas Heart Institute scoring method for endomyocardial biopsies. Grades 1-3: mild; 4-6: moderate; and 7-10: severe [see McAllister et al.: A system for grading cardiac allograft rejection. Texas Heart Institute J. 13, 1 (1986)].
NS = not significant.

IV. Effect of "maintenance" cyclosporin treatment on IFN-γ mediated induction of oxidative burst of neutrophils by FMLP Lewis rats on the "maintenance" cyclosporin regimen described above received a heart transplant from AC rats. All rats received 20 mg/kg/day cyclosporin beginning on the day of transplantation and continuing for 2 additional days. The rats also received a "maintenance" dose of 8/mg/kg/day cyclosporin beginning on the third day of post-transplantation and continuing until sacrifice of the animals, and were sacrificed 4 days post-transplantation. The rats received a high dose of 75,000 units of IFN-γ via the intramuscular route starting on the day of transplantation and for three additional days. After four days, the rats were sacrificed and bled, and their neutrophils were tested for the IFN-γ mediated FMLP-induced oxidative burst. Two experiments were performed using two rats each. The data presented in Table 4 suggest that the "maintenance" cyclosporin did not inhibit the IFN-γ mediated production of superoxide by neutrophils.

TABLE 4

Effect of "maintenance" cyclosporin treatment on FMLP induced oxidative burst of neutrophils from animals that received IFN-γ

| Treatment | N | Superoxide Generated (nm/$10^6$ Cells) |
|---|---|---|
| Control | 2 | (in duplicate) 0.68 |
| 75,000 u IFN-γ | 2 | (in duplicate) 3.70 |

V. Discussion

Treatment of rats with a heterologous heart-transplant with IFN-γ has been shown to increase the rate of rejection of the heart in the current study. The time to rejection was decreased from 44.7 days to 11 days. This suggests that IFN-γ treatment for infection during transplantation could affect dramatically the outcome of the transplantation. The enhanced rejection could be due to increased induction of histocompatibility antigens, particularly class II histocompatibility antigens, by the IFN-γ treatment. However, since IFN-γ has a multitude of immunoregulatory activities, it is possible that the IFN-γ could be affecting rejection by other, as yet undefined, mechanisms. The mechanisms of how IFN-γ enhances rejection remain to be established in future studies.

In any case, the results of the current study suggest that the potential deleterious effects of utilizing IFN-γ in transplant patients can be avoided. Use of continuous, low "maintenance" doses of cyclosporin throughout the study period, as carried out for extended periods of time on most transplant patients, resulted in an abrogation of the deleterious effects of the IFN-γ treatment on the transplanted heart. Therefore, it is possible to administer IFN-γ to transplanted individuals via a systemic route without inducing rejection of the transplanted tissue. This makes even more attractive the potential use of IFN-γ administration via a local route (such as aerosolization) to transplant patients.

Since cyclosporin is a generally immunosuppressive drug, the question could be asked: if "maintenance" cyclosporin treatment results in abrogation of IFN-γ-induced enhanced heart transplant rejection, does it also abrogate the beneficial antimicrobial effects of the IFN-γ treatment? The results of the present study suggest that this is not the case. "Maintenance" cyclosporin therapy did not alter the enhanced FMLP-induced oxidative burst of neutrophil from animals that had received IFN-γ. Since the neutrophil is a major cell for combatting infections, these results suggest that at least some of the positive anti-microbial benefits of the potential IFN-γ treatment of transplanted individuals would be retained using "maintenance" cyclosporin therapy.

EXAMPLE 2

The effect of IFN-γ in the mouse autologous bone marrow transplant model

In this model, adult male CBA/J mice, weighing 20-25 g each, (Jackson Laboratories, Bar Harbor, Me.) are lethally irradiated with 900 rads of X-irradiation. The mice are then reconstituted on the same day with approximately $1 \times 10^7$ bone marrow cells obtained from the femurs and tibia of normal CBA/J donor mice. The mice are maintained on acidified water in a clean environment, and several survive for at least 2-3 weeks after transplantation. The mice receive 20 mg/kg/day cyclosporin beginning on the day of bone marrow transplantation and continuing for two additional days. The mice also receive "maintenance" doses of 8 mg/kg/day of cyclosporin beginning on the third day post-transplantation and continuing until sacrifice. Experimental mice are treated with either 750 units/day or 7,500 units/day of recombinant murine IFN-γ (a gift of Genentech, Inc., South San Francisco, Calif. The specific activity of this IFN-γ is approximately $2.3 \times 10^7$ units/mg protein and is diluted with RPMI-1640 medium (Gibco Laboratories, Grand Island, N.Y.)) via the intramuscular route starting on the day of bone marrow transplantation and for three additional days. In one set of experiments, survival of the mice is determined over a three-week period. Peripheral complete blood counts are performed on a regular basis to determine success of engraftment. In addition, members of the IFN-γ treated and of the control groups are sacrificed 1-2 times weekly, and bone marrow examined for success of engraftment. When the animals die, they are examined for evidence of infection. Levels of Ia antigen expression on peripheral blood lymphocytes are determined by specific-antibody staining and flow cytometry one day prior to transplant and on days 1, 7, and 14 post-transplant. A comparison of the complete blood count and survival rate between control and treated groups shows the effect of IFN-γ treatment on the course of autologous bone marrow transplantation.

EXAMPLE 3

The effect of IFN-γ treatment on exogenously induced infection in transplant patients The ability of IFN-γ treatment to affect the survival rate of transplanted rodents that are infected deliberately is examined in the cardiac allograft and autologous bone marrow transplant models described in Examples 1 and 2. Lengths of 3-0 twisted cotton suture are incubated overnight in trypticase soy broth (BBL Microbiological Systems, Cockeysville, Md.) and inoculated with *Klebsiella pneumoniae* (Capsular Type 2). On the third day after transplantation, lengths of suture attached to a French eye needle are inserted aseptically into the right thigh of each rodent and the suture is cut flush with the skin at either end buried subcutaneously. A group of transplanted rodents in each model are treated with IFN-γ essentially as described in Examples 1 and 2 hereinabove. Another group is sham-treated with diluent. Rodents are monitored for 2-3 weeks. Bacterial blood cultures are carried out on alternate days. Uninfected transplanted rodents serve as a control to insure that complications of transplantation procedure are not responsible for animal mortality. Efficacy of IFN-γ treatment is determined by observation of increased survival and by analysis of blood cultures. At the time of death, all animals undergo necropsy with careful examination for signs of pneumonitis, peritonitis, and endocarditis.

All citations cited throughout the specification, and the references cited therein, are hereby expressly incorporated by reference.

The foregoing description details methods and compositions representative of the present invention. It is understood that modifications and variations are possible without departing from the general concept of the present invention, and that such modifications are intended to be within the scope of the present invention.

We claim:

1. A method for the prophylaxis or treatment of microbial infections in transplant recipients comprising administering a therapeutically effective dose of interferon-γ (IFN-γ) or interleukin-2 (IL-2) or a combination thereof to transplant recipients subjected to maintenance immunosuppressive therapy comprising the administration of a cyclosporin following transplantation.

2. The method of claim 1 wherein said cyclosporin is Cyclosporin A.

3. The method of claim 2 wherein Cyclosporin A is administered in a postoperative dose of about from 1 to 20 mg/kg of body weight/day.

4. The method of claim 1 wherein IFN-γ is administered prophylactically.

5. The method of claim 4 wherein IFN-γ administration is initiated within about 40 days following transplantation.

6. The method of claim 5 wherein IFN-γ administration is initiated immediately following transplantation.

7. The method of claim 5 wherein IFN-γ administration is maintained essentially during the entire hospitalization of said transplant recipient.

8. The method of claim 5 comprising the administration of Cyclosporin A parallel with IFN-γ administration 9. The method of claim 8 wherein a biological response modifying level of Cyclosporin A is maintained for at least the duration of IFN-γ administration.

10. The method of claim 9 wherein said Cyclosporin A is administered in a dose of about from 1 to 20 mg/kg of body weight/day.

11. The method of claim 4 wherein said transplant recipient is not known to have a tumor or an intracellular infection.

12. The method of claim 1 wherein the IFN-γ administration is initiated subsequent to the onset of said microbial infection.

13. The method of claim 12 wherein at least one causative organism of said microbial infection is selected from the group consisting of bacteria, fungi, viruses and parasites.

14. The method of claim 13 wherein said organism is *Pneumocystis carinii, Legionella* species, *Salmonella* species, *Lysteria monocytogenes,* Cytomegalovirus (CMV) or Epstein-Barr (E-B) virus.

15. The method of claim 14 wherein IFN-γ is administered for at least about 14 days following the diagnosis of said microbial infection.

16. The method of claim 15 wherein IFN-γ is administered in daily to once a week intervals.

17. The method of claim 12 wherein said maintenance immunosuppressive therapy comprises the administration of Cyclosporin A.

18. The method of claim 17 wherein the administration of a biological response modifying dose of Cyclosporin A is maintained for the rest of the lifetime of said transplant recipient.

19. The method of claim 18 further comprising the step of monitoring a parameter or symptom indicating the onset of a rejection episode.

20. The method of claim 19 wherein the administration of a steroid and IFN-γ is initiated when said monitoring indicates the onset of rejection.

21. The method of claim 20 wherein IFN-γ administration is maintained for about two weeks.

22. The method of claim 4 wherein said IFN-γ is administered in the form of a liquid pharmaceutical composition.

23. The method of claim 22 wherein said liquid pharmaceutical composition has a pH of about 4.0 to 6.0, and comprises a stabilizing agent and a non-ionic detergent.

24. The method of claim 4 wherein said IFN-γ is administered by intrapulmonary delivery of a dispersion of a therapeutically effective amount thereof.

25. The method of claim 12 wherein said IFN-γ is administered in the form of a liquid pharmaceutical composition.

26. The method of claim 25 wherein said liquid pharmaceutical composition has a pH of about 4.0 to 6.0, and comprises a stabilizing agent and a non-ionic detergent.

27. The method of claim 12 wherein said infection is a lung infection, and said IFN-γ is administered by intrapulmonary delivery of a dispersion of a therapeutically effective amount thereof.

28. The method of claim 32 wherein in said dispersion greater than about 15% of the particles have a particle size of from about 0.5 μm to about 4 μm.

29. The method of claim 4 wherein said IFN-γ is desCysTyrCys human IFN-γ.

30. The method of claim 29 wherein said IFN-γ lacks the last 4 C-terminal amino acid residues.

31. The method of claim 12 wherein said IFN-γ is desCysTyrCys human IFN-γ.

32. The method of claim 31 wherein said IFN-γ lacks the last 4 C-terminal amino acid residues.

33. A method of avoiding infection-associated graft rejection in transplant recipients, comprising administering a therapeutically effective dose of IFN-γ to transplant recipients subjected to maintenance immunosuppressive therapy comprising the administration of a cyclosporine following transplantation.

* * * * *